United States Patent [19]

Barbour et al.

[11] 4,435,568

[45] Mar. 6, 1984

[54] THIOL METHYLATION PROCESS-REACTION, RECYCLE AND REGENERATION OF METHYL BROMIDE

[75] Inventors: Kenneth L. Barbour, Newark; William L. Geigle, New Castle, both of Del.; Frank R. Haglid, deceased, late of Wilmington, Del., by Britt I. Haglid, executrix

[73] Assignee: E. I. Du Pont de Nemours and Company, Wilmington, Del.

[21] Appl. No.: 400,756

[22] Filed: Jul. 22, 1982

[51] Int. Cl.³ ............................................ C07D 253/06
[52] U.S. Cl. ................................................... 544/182
[58] Field of Search ......................................... 544/182

[56] References Cited

U.S. PATENT DOCUMENTS

| | | | |
|---|---|---|---|
| 3,890,317 | 6/1975 | Haglid | 260/249.5 |
| 3,897,429 | 7/1975 | Haglid | 260/248 |
| 3,905,973 | 9/1975 | Gobeil et al. | 260/248 |
| 4,035,364 | 7/1977 | Dickore et al. | 260/248 |
| 4,328,340 | 5/1982 | Bonse et al. | 544/182 |

*Primary Examiner*—John M. Ford

[57] ABSTRACT

The process of thiol methylation of butylthion using methyl bromide to produce metribuzin has been significantly improved by the development of a reaction temperature profile, the recycle of methylation process reaction supernatant, and new conditions for the regeneration of methyl bromide from used methylation process reaction supernatant.

8 Claims, No Drawings

THIOL METHYLATION PROCESS-REACTION, RECYCLE AND REGENERATION OF METHYL BROMIDE

TECHNICAL FIELD

This invention relates to improvements in the process of methylation of 4-amino-6-t-butyl-3-mercapto-1,2,4-triazin-5-one, hereinafter referred to as butylthion, using methyl bromide to produce 4-amino-6-t-butyl-3-methylmercapto-1,2,4-triazin-5-one, hereinafter referred to as metribuzin.

BACKGROUND OF THE INVENTION

Metribuzin is produced commercially in large quantities and extensively used as a herbicide for undesired vegetation associated with soybeans. Preventing or minimizing loss of a portion of such a valuable crop, with over 60 million metric tons annual production [Sci. Amer., 235, 88 (1976)], by inhibiting the growth or killing undesired competing vegetation, is a significant approach to improving agricultural efficiency. More than 25 million acres under soybean cultivation are estimated to have utilized a weed control program incorporating metribuzin in 1981.

U.S. Pat. No. 3,905,973 discloses the methylation of butylthion to yield metribuzin using methyl chloride as the methylating agent in the presence of iodide ion. The required use of iodide compounds does not enable the greatest economy, and a mixture of methyl isomers is produced which reduces the yield of active product.

U.S. Pat. No. 3,897,429 discloses the methylation of butylthion using methyl bromide in water or in aqueous alcohol, ketone, or amide solutions at a single temperature in the range $-15°$ C. to $+30°$ C. in the presence of alkali metal hydroxide utilizing a single contacting of the reagents to make metribuzin. Mixtures of water and organic solvents are only proposed to maintain a liquid phase if a reaction temperature below $0°$ C. is used. The patent further discloses the regeneration of methyl bromide by reaction of used process supernatant with methyl alcohol and sulfuric acid in a 15–25% excess after first removing water by distillation to concentrate the sodium bromide solution produced by the reaction of butylthion with methyl bromide in the presence of sodium hydroxide. The regenerated methyl bromide is then reused directly in a subsequent methylation reaction. It has now been discovered that a greater yield and purity of metribuzin can be achieved using a temperature profile during the reaction of butylthion and methyl bromide, and that even greater economy can be achieved by regenerating methyl bromide with a greater excess of sulfuric acid.

U.S. Pat. No. 4,035,364 discloses modifications in the basic process of methylation of butylthion claimed in the '429 patent described above. In particular, the patent discloses reaction in aqueous media in the substantial absence of air, the use of alkyl aryl polyglycol ether emulsifier, and the possible one-time partial reuse of methylation process reagents. The procedure disclosed for regeneration of methyl bromide involves concentrating all solutions to dryness and subsequently reacting solid sodium bromide with methanol and sulfuric acid. Partial, one-time reuse of methylation process reagents does not achieve maximum economy, or produce a sufficiently high concentration of sodium bromide to reduce evaporative energy requirements during methyl bromide regeneration. In addition, evaporation of the reaction supernatant to dryness prior to methyl bromide regeneration is wasteful of energy.

U.S. Pat. No. 3,890,317 discloses the methylation of butylthion using process equipment including a filter or a centrifuge to enable continuous removal of metribuzin from the reaction mixture using water as the preferred solvent. The process disclosed can operate in either a batch or continuous mode.

SUMMARY OF THE INVENTION

It has now been found that new techniques and process parameters removed from those currently known can result in significant improvements in the production of metribuzin. Specifically, in the process of contacting and reacting butylthion with methyl bromide in aqueous alkaline solution to form a reaction mixture from which metribuzin precipitates and is recovered leaving a reaction supernatant containing methyl bromide, butylthion, and alkali metal bromide, the improvement comprising carrying out the reaction with a temperature profile in which methyl bromide addition and initial reaction occur at one temperature, followed by increasing the temperature and maintaining it for additional reaction to enhance the purity and yield of said metribuzin over that obtained by carrying out the entire reaction at the first or second temperature. Another aspect of this invention consists of the improvement comprising repeating said process at least one time but using the previously resulting reaction supernatant as said reaction mixture for subsequent contacting and reacting of virgin butylthion and methyl bromide. And finally, still another aspect of the invention consists of the improvement comprising the regeneration of methyl bromide from said reaction supernatant by increasing the alkali metal bromide concentration to 45–55% weight by removing water, and contacting and reacting the resulting concentrated reaction supernatant with methanol and an excess of sulfuric acid in the mole ratio of sulfuric acid to alkali metal bromide in the range of about 1.4–1.6.

The use of a temperature profile during the reaction of butylthion with methyl bromide, the repeated reuse of methylation process reagents, and the use of modified conditions for regeneration of methyl bromide from used methylation process reagents can significantly improve the yield and purity of metribuzin, reduce the cycle time necessary for reaction, eliminate butylthion recovery operations, and reduce costly energy consumption in methyl bromide regeneration.

DETAILED DESCRIPTION OF THE INVENTION

A. Methylation Reaction Temperature Profile

The addition of methyl bromide to aqueous solutions of butylthion at $100°$ C. and subsequently increasing the temperature to $20°$ C. to continue the reaction results initially in good solubility of methyl bromide and a favorable ratio of metribuzin to the less desirable competing reaction product 4-amino-6-t-butyl-2-methyl-3-thio-1,2,4-triazin-3,5-dione (hereinafter referred to as the N-methyl isomer), while the subsequent reaction at the higher temperature reduces the required time for completeness of reaction, increases the conversion of butylthion to metribuzin, and enhances handling of the product slurry by insuring its fluidity. The initial temperature of the profile, $10°$ C., was selected on the basis that initial reaction at $10°$ C. suppresses the formation of the N-methyl isomer and provides good solubility of methyl bromide, while still insuring fluidity of the liquid phase and an economically reasonable reaction time. the second temperature of the profile, 20° C., was selected as one which reduces overall reaction time, gives more complete conversion of butylthion to metribuzin while maintaining purity, and enhances product slurry fluidity. The use of a temperature profile involving 10° C. and 20° C. has been unexpectedly found to produce a greater yield of metribuzin for a given reaction time than at either single temperature.

As indicated in U.S. Pat. No. 3,897,429, the disclosure of which is hereby incorporated by reference, the methylation of butylthion (Compound A of the '429 Patent) can be carried out in water, or mixtures of water and an organic liquid such as methanol, ethanol, isopropanol, acetone, methyl ethyl ketone, and dimethylformamide. Unlike the prior art which utilized methanol only to maintain a liquid phase at temperatures less than 0° C., methanol in mixture with water has been found to be effective as an emulsifier to insure stability of reaction suspensions, especially at the high sodium bromide concentrations produced by the recycling of reaction mixture supernatant and effective in reducing the water content in the filter cake of metribuzin (Compound B of the '429 Patent). In accordance with the present invention, 4%±1% methanol has been determined to be most effective. Greater amounts can render the slurry unstable.

The reaction temperature profile found to provide the greatest yield of metribuzin involves initial addition of methyl bromide to a 4% aqueous methanol solution of butylthion at a pH in the range 11-12 at 10° C. over a period of one hour. The methyl bromide is effectively kept in solution with the aid of a refrigerated condenser. The temperature is then raised to 20° C. over no less than 10 minutes and no more than 30 minutes, and held at 20° C. for between 1 and 4 hours to continue the methylation reaction. Metribuzin can be isolated from the product slurry by filtration or centrifugation.

The reaction is conducted at a pH in the range of 10-14, preferably at a pH of 11 to 12. While both sodium hydroxide or potassium hydroxide can be utilized to adjust and control the pH, sodium hydroxide is preferred because of cost. Where reuse of the reaction supernatant in additional cycles of contacting virgin butylthion is desired, the initial concentration of sodium bromide can be adjusted to a maximum of 15% by addition of the solid salt. This concentration of sodium bromide results in a stable product suspension after further increase in concentration due to the formation of additional sodium bromide during reaction of methyl bromide with butylthion in aqueous alkaline solution, a reduction in the amount of water to be removed by distillation prior to regeneration of methyl bromide, as well as immediately bringing the sodium bromide concentration to the desired level for recycle of reaction supernatant so that known, constant amounts of water and methanol can be added to maintain the desired concentrations for every cycle of reuse.

B. Recycle of Reactive Supernatant

Reuse of the reaction supernatant resulting after filtration or centrifugation of metribuzin from the reaction mixture for subsequent contacting and reaction of virgin butylthion and virgin methyl bromide, materials which have not been previously used in the methylation reaction, is advantageous in that the concentration of alkali metal bromide builds up so that the amount of water to be removed by distillation prior to regeneration of methyl bromide is significantly reduced. Surprisingly, extensive studies have established the unpredictable finding that the maximum concentration of sodium bromide and methanol is 18% and 8%, respectively, before the reaction mixture becomes unstable and aggregates. By recycling approximately two thirds of the reaction supernatant and readjusting the sodium bromide and methanol concentrations by adding water and methanol, the reaction supernatant can be maintained at 15% sodium bromide and 4% methanol and recycled numerous times.

C. Regeneration of Methyl Bromide

After removal of metribuzin from the reaction mixture by centrifugation or filtration, the resulting reaction supernatant is concentrated by removal of water by distillation at atmospheric or reduced pressure to a water content of 45-50%. Since the reaction supernatant is about 18% sodium bromide, less water need be distilled out. At lower water concentrations, a thick slurry results, representing agitation problems.

Methanol, at a molar ratio to sodium bromide in the range of 1.1 to 1.2, and concentrated sulfuric acid at a molar ratio to sodium bromide in the range of 1.4 to 1.6 are added to the concentrated alkali metal bromide solution. The unpredictable optimum condition of 50% excess sulfuric acid was discovered by balancing the heating/cooling load (proportional to the reaction time) and the yield of methyl bromide, and the cost of additional raw materials. At a mole ratio of 1.4 to 1.6 for sulfuric acid, one achieves the most favorable balance of heating and cooling load, material feed, cost, waste treatment, and waste disposal. The heat of hydration for the sulfuric acid is initially used as a source of heat to distill methyl bromide from the reaction vessel thereby minimizing energy consumption. Heating is then commenced and methyl bromide distillation continued. The reflux to distillate ratio is increased stepwise from 1 to 10 to obtain essentially pure methyl bromide overhead. Distillation time is approximately 1.5 to 2.0 hours. At mole ratios of sulfuric acid of 1.2 and 1.8, the methyl bromide regeneration time is about four and one hours, respectively.

EXAMPLES

Unless specified otherwise, in all statements of process conditions, temperature is expressed in °C. with a ±2° C. experimental limit of error, and concentrations referred to as percentages (%) are by weight or parts by weight.

EXAMPLE 1

A solution was prepared by dissolving 100 parts by weight butylthion in a solution containing 360 parts water, 16 parts methanol, and 40 parts 50% sodium hydroxide. The resulting solution was cooled to 10° C. and adjusted and maintained at pH 11.5 with sodium hydroxide. To the above solution was added 51 parts methyl bromide as a liquid over one hour while maintaining a temperature of 10° C. and pH 11.5. When methyl bromide addition was complete, the temperature of the solution was raised to 20° C. within 10-20 minutes and held for three hours at pH 11.5. The reaction mixture was centrifuged to recover 96.9 parts of metribuzin which was washed with 100 parts water. The reaction supernatant resulting from the centrifugation was subsequently utilized for additional reaction and/or regeneration of methyl bromide.

EXAMPLE 2

A solution was prepared by dissolving 100 parts by weight butylthion in a solution consisting of 500 parts water, 21 parts methanol, 38 parts 50% sodium hydroxide, and 92 parts sodium bromide. The resulting solution was cooled to 10° C. and adjusted to and maintained at pH 11.5 with 4 N sodium hydroxide. To this solution, 54 parts of methyl bromide were added as a liquid over one hour while maintaining a temperature of 10° C. and pH 11.5. The temperature of the reaction mixture was then increased to 20° C. over a 20 minute period and held for one hour at pH 11.5. The reaction mixture was centrifuged and the product washed with 100 parts of water to recover 94.3 parts metribuzin.

EXAMPLE 3

To recycle the reaction supernatant, 105 parts water, 8 parts methanol, and 38 parts 50% sodium hydroxide were added to 500 parts recycled reaction supernatant initially containing 17.1% sodium bromide and 2.5% methanol. One hundred (100) parts of butylthion were added to the solution, it was cooled to 10° C., and the pH adjusted and maintained at 11.5 with 4 N sodium hydroxide. To this solution was added 51 parts of methyl bromide as a liquid over one hour while maintaining a temperature of 10° C. and pH 11.5. When methyl bromide addition was complete, the temperature was then increased to 20° C. over a 20 minute period and held for one hour at pH 11.5. The reaction mixture was then centrifuged and the product washed with 100 parts water to recover 94.4 parts metribuzin.

EXAMPLE 4

Recycled reaction supernatant initially about 18% by weight sodium bromide was concentrated to 55% by weight sodium bromide. For the regeneration of methyl bromide, 187 parts of the above warm sodium bromide concentrate and 38.5 parts methanol were combined and transferred to a batch distillation apparatus consisting of a pot, packed column, refrigerated overhead total condenser, and reflux splitter. A total of 155 parts 96% sulfuric was added dropwise to the warm solution (40° C.–60° C.) to increase the pot temperature to 70° C.–80° C. When approximately one half of the sulfuric acid had been added, methyl bromide began to distill overhead. The reflux to distillate ratio was increased stepwise from 1 to 10. When the overhead temperature rose, about 70 minutes after the initial addition of sulfuric acid, the column was returned to total reflux. After the overhead temperature decreased in about 20 minutes, a final portion of methyl bromide was distilled out. Distillation was continued briefly to remove a methyl bromide-methanol mixture. The total recovery of methyl bromide was 92.5 parts.

It will be apparent that the instant specification and examples are set forth by way of illustration and not limitation, and that various modifications and changes may be made without departing from the spirit and scope of the present invention.

We claim:

1. In the process of contacting and reacting butylthion with methyl bromide in aqueous alkaline solution to form a reaction mixture from which metribuzin precipitates and is recovered leaving a reaction supernatant containing methyl bromide, butylthion, and alkali metal bromide, the improvement comprising carrying out the reaction with a temperature profile in which methyl bromide addition and initial reaction occur at one temperature, followed by increasing the temperature and maintaining it for additional reaction.

2. The process of claim 1 wherein said one temperature is about 10° C. and the second mentioned temperature is about 20° C.

3. In the process of claim 1, the improvement further comprising (a) adding sodium bromide to said aqueous alkaline solution to produce an initial concentration of sodium bromide of 15% by weight; (b) adding methanol to said aqueous alkaline solution to produce an initial concentration of methanol of 4% by weight; (c) adding methyl bromide to said aqueous alkaline solution at 10° C.±2° C. over a period of one hour for contacting and reacting; (d) increasing the temperature to 20° C.±2° C. over a period of from 10 to 30 minutes for subsequent contacting and reacting for up to four hours; and (e) adjusting and maintaining the pH of said reaction mixture at a pH of between 11 and 12 by adding sodium hydroxide.

4. In the process of contacting and reacting butylthion with methyl bromide in aqueous alkaline solution to form a reaction mixture from which metribuzin precipitates and is recovered leaving a reaction supernatant containing methyl bromide, butylthion, and alkali metal bromide, the improvement comprising repeating said process at least one time using the previously resulting reaction supernatant as said reaction mixture for subsequent contacting and reacting of virgin butylthion and methyl bromide and for each cycle of repeating said process (a) reusing about two thirds of said reaction supernatant for contacting and reacting with virgin butylthion and methyl bromide while one third is utilized for methyl bromide regeneration; (b) adding water to said reaction supernatant to adjust the sodium bromide concentration to 15% by weight prior to addition of virgin butylthion and methyl bromide; and (c) adding methanol to said reaction supernatant to adjust methanol concentration to 4% by weight prior to addition of virgin butylthion and methyl bromide.

5. In the process of contacting and reacting butylthion with methyl bromide in aqueous alkaline solution to form a reaction mixture from which metribuzin precipitates and is recovered leaving a reaction supernatant containing methyl bromide, butylthion and alkali metal bromide, the improvement comprising regenerating methyl bromide from said reaction supernatant by (a) increasing the alkali metal bromide concentration to 45–55% by weight by removing water, and (b) contacting and reacting the resulting concentrated reaction supernatant with methanol and an excess of sulfuric acid in the mole ratio of sulfuric acid to alkali metal bromide in the range of about 1.4–1.6.

6. The process of claim 5 wherein the concentration of sodium bromide in the reaction supernatant is increased to a range from 50–55% by the removal of water by distillation.

7. In the process of contacting and reacting butylthion with methyl bromide in aqueous alkaline solution to form a reaction mixture from which metribuzin precipitates and is recovered leaving a reaction supernatant containing methyl bromide, butylthion, and alkali metal bromide, the improvement comprising (a) utilizing a temperature profile in which methyl bromide addition and initial reaction occur at one temperature, followed by increasing the temperature and then maintaining it for additional reaction, (b) repeating said process but using the previously resulting reaction supernatant as said reaction mixture for subsequent contacting and reacting of virgin butylthion and methyl bromide, and (c) regenerating methyl bromide from said reaction supernatant by increasing the alkali metal bromide concentration to 45–55% weight by removing water, and contacting and reacting the resulting concentrated reaction supernatant with methanol and an excess of sulfuric acid in the mole ratio of sulfuric acid to alkali metal bromide in the range of about 1.4–1.6.

8. Improved process of claim 7 wherein (a) methyl bromide is added to the reaction solution at a temperature of 10° C. over a period of one hour; (b) followed by increasing the temperature to 20° C. over a period of 10 to 30 minutes for subsequent contacting and reaction for up to four hours; (c) the solvent for butylthion-methyl bromide reaction is 4% methanol in water; (d) a pH of between 11 and 12 adjusted and maintained by sodium hydroxide; (e) the reaction solution is initially made 15% sodium bromide by addition of sodium bromide; (f) about two thirds of said reaction supernatant is reused as said reaction mixture for contacting and reacting virgin butylthion and methyl bromide while one third is utilized for methyl bromide regeneration; (g) water is added to said reused reaction supernatant to adjust the sodium bromide concentration to 15% prior to addition of virgin butylthion and methyl bromide; (h) methanol is added to said reused reaction supernatant to adjust methanol concentration to 4% prior to addition of virgin butylthion and methyl bromide; (i) for regeneration the concentration of sodium bromide in the reaction supernatant is increased to a range from 50–55% by the removal of water by distillation, and (j) the concentrated reaction supernatant is contacted with a molar excess of sulfur acid to sodium bromide in the range of 1.4 to 1.6 to regenerate methyl bromide.

* * * * *